United States Patent [19]

Jiles et al.

[11] Patent Number: 5,475,305
[45] Date of Patent: Dec. 12, 1995

[54] MAGNETIC INSPECTION PROBE FOR MEASUREMENT OF MAGNETIC ANISOTROPY

[75] Inventors: David C. Jiles; Michael K. Devine, both of Ames, Iowa

[73] Assignee: Iowa State University Research Foundation, Inc., Ames, Iowa

[21] Appl. No.: 19,079

[22] Filed: Feb. 18, 1993

[51] Int. Cl.$^6$ .......................... G01R 33/12; G01R 33/02; G01B 7/24; G01N 27/72
[52] U.S. Cl. .......................... 324/227; 324/247; 324/209; 324/243
[58] Field of Search .................................. 324/200, 209, 324/225, 226, 228, 232, 242, 243, 244, 247, 251, 262

[56] References Cited

U.S. PATENT DOCUMENTS

| | | | |
|---|---|---|---|
| 3,109,139 | 10/1953 | Branker | 324/240 |
| 3,311,818 | 3/1967 | Quittner | 324/209 |
| 3,427,872 | 2/1969 | Leep et al. | 73/779 |
| 3,612,986 | 10/1971 | Rollwitz et al. | 324/209 |
| 3,742,357 | 6/1973 | Kubo et al. | 324/209 |
| 3,861,206 | 1/1975 | Kawafune et al. | 73/862.336 |
| 3,925,724 | 12/1975 | Steingroever | 324/243 |
| 3,976,935 | 8/1976 | Steingroever | 324/316 |
| 4,095,181 | 2/1982 | Jilken | 324/209 |
| 4,316,146 | 2/1982 | Harris et al. | 324/238 |
| 4,379,261 | 4/1983 | Lakin | 324/240 |
| 4,463,313 | 7/1984 | Steingroever et al. | 324/243 |
| 4,495,466 | 1/1985 | Lakin | 324/242 |
| 4,528,856 | 7/1985 | Junker et al. | 73/779 |
| 4,534,405 | 8/1985 | Hulek et al. | 164/451 |
| 4,634,976 | 1/1987 | Tiitto | 324/240 |
| 4,789,827 | 12/1988 | Bergannder | 324/242 |
| 4,881,030 | 11/1989 | Stuecker et al. | 324/209 |
| 5,008,621 | 4/1991 | Jiles | 324/227 |
| 5,010,299 | 4/1991 | Nishizawa et al. | 324/209 |
| 5,012,189 | 4/1991 | Jiles | 324/209 |
| 5,059,903 | 10/1991 | Otaka et al. | 324/223 |
| 5,241,270 | 8/1993 | Ng | 324/251 |
| 5,293,117 | 3/1994 | Hwang | 324/242 |

FOREIGN PATENT DOCUMENTS

| | | | |
|---|---|---|---|
| 0593131 | 2/1978 | U.S.S.R. | 324/251 |
| 0930179 | 5/1982 | U.S.S.R. | 324/251 |
| 0194932 | 9/1986 | U.S.S.R. | 324/251 |

OTHER PUBLICATIONS

"Effects of Grain Size, Hardness, and Stress on the Magnetic Hysteresis Loops of Ferromagnetic Steels," by Kwun et al., J. Appl. Phys. 61(4), 15 Feb. 1987, pp. 1567–1579.

Primary Examiner—Sandra L. O'Shea
Assistant Examiner—Jay M. Patidar
Attorney, Agent, or Firm—Leydig, Voit & Mayer

[57] ABSTRACT

A magnetic inspection probe for use in the planar measurement of magnetic properties in two or more defined directions. The inspection probe includes a cup-shaped outer body, a centrally disposed central core, a field generating power coil, a flux coil for measuring magnetic induction and a plurality of field detection elements disposed in various known orientations. In use, the inspection probe of the present invention permits the detection and measurement of anisotropy of material characteristics in at least two directions across the plane of measurement.

15 Claims, 1 Drawing Sheet

MAGNETIC INSPECTION PROBE FOR MEASUREMENT OF MAGNETIC ANISOTROPY

GRANT REFERENCE

This invention was made with Government support under Contract No. ITA87-02 awarded by the U.S. Department of Commerce. The Government has certain rights in the invention.

FIELD OF THE INVENTION

The present invention relates generally to magnetic inspection probes and more particularly to a magnetic inspection probe for use in identification and measurement of in-plane anisotropy in a material specimen.

BACKGROUND OF THE INVENTION

It is common for anisotropy to exist across the surface of structural materials. For example, the stress levels in a steel plate which has undergone directional work, such as rolling, will typically vary substantially when measured in different directions across the surface of the plate. Such anisotropy in the planar stress of a material is commonly referred to as biaxial stress and may be represented in a well known manner by two orthogonal stress vectors $\sigma_x$ and $\sigma_y$. Likewise, when a specimen has been subjected to directional loading, there will be anisotropy in the magnetic properties. In addition, the microstructure of the plate material may also vary in a directional manner across the surface.

Prior to the present invention, magnetic inspection probes have typically consisted of a substantially "C" shaped core wrapped with a power coil thereby generating a magnetic field in only one direction in the test specimen. An inspection apparatus utilizing one such uni-directional probe is illustrated in K. Kwun and G. L. Burkhardt, "Effects of Grain Size, Hardness, and Stress on the Magnetic Hysteresis Loops of Ferromagnetic Steels," *J. Appl. Phys.*, Vol. 61, No. 4 (1987). As will be appreciated, in order to measure directional variations in the magnetic properties of a material, such a uni-directional probe must be reoriented with respect to the surface of the sample before each measurement is taken.

The magnetic inspection probe of the present invention is particularly useful in the evaluation of biaxial stress. However, anisotropy with respect to other physical characteristics—for example, texture or preferred grain orientation—may also be evaluated. Methods for measuring the physical characteristics of a material by means of magnetic evaluation have recently become known in the art. For example, U.S. Pat. No. 5,008,621 to Jiles discloses a system and method for use in the evaluation of the bulk magnetic properties of a material to obtain meaningful information regarding intrinsic physical characteristics.

The system of the '621 patent subjects a sample of a material to a magnetic field and takes multiple measurements of the magnetic field and magnetic flux of the specimen as the magnetic field is cycled in a controlled manner. As will be recognized, such a controlled cycling permits the collection of data sufficient to generate a magnetic hysteresis curve. As is well known, the magnetic hysteresis curve is a plot of flux density B in a material versus a varying applied magnetic field intensity H.

From the features of the hysteresis curve, an evaluation of the physical properties of a material can be made. For example, it is known that coercivity can be used to detect plastic deformation and hardness, that maximum differential permeability can be used to measure stress, that a combination of remanence and coercivity can be used to detect impending fatigue failure and that hysteresis loss can be used to detect changes in grain boundary segregation arising from temper embrittlement.

The system and method of the '621 patent to Jiles are useful in evaluating the overall bulk properties of a material. However, because the measurements taken with regard to specimen flux and field intensity have no specific directional component, directional anisotropy in features such as stress or microstructure is not identified.

U.S. Pat. No. 5,012,189 also to Jiles discloses a specific method for deriving information regarding stress from a ferromagnetic material. Specifically, the '189 patent discloses the ability to derive a meaningful estimate of the actual and residual stress occurring in a material based on the hysteresis and anhysteretic magnetization curves at the origin as compared to such curves in an unstressed sample. While the method for stress evaluation disclosed in the '189 patent is of great use, and is incorporated herein by reference, no means is disclosed therein for measuring any directional variation in stress or other intrinsic properties.

U.S. Pat. No. 5,059,903 to Otaka et al. discloses a system and method for evaluation of the embrittlement of a material through comparison of the magnitude of magnetization characteristics measured in a sample specimen to the magnetic characteristics of a virgin specimen. By making these analyses on a periodic basis, it is possible to determine degradation rates as well as to identify areas in which degradation is most severe.

While the '903 patent to Otaka et al. is useful in determining the location of degradation, no means is provided which would be capable of measuring in-plane anisotropy without taking multiple measurements in different directions.

SUMMARY OF THE INVENTION

In view of the foregoing, it is a general object of the present invention to provide a magnetic inspection probe which can efficiently take magnetic measurements capable of characterizing anisotropic properties in a magnetic material.

In that respect, it is an object of the present invention to provide a magnetic inspection probe which allows the measurement of magnetic properties in two or more directions which are oriented in a known manner along a specimen surface without the need to neorient the probe to obtain each directional measurement.

It is a related object of the present invention to provide a magnetic inspection probe which allows the measurement of magnetic properties in two orthogonal directions without movement of the probe.

It is a further related object of the present invention to provide a magnetic inspection probe which allows the measurement of biaxial stress without movement of the probe.

Accordingly, it is a feature of the present invention to provide an inspection probe which can be placed at a location on the surface of a material having anisotropic magnetic properties and can take a reading at that location to derive sufficient information to characterize the magnetic properties of the material at that location including any directional variation therein.

It is a subsidiary feature of the present invention to provide a magnetic inspection probe which may be moved across the surface of a material measuring flux density and field intensity in at least two related directions at various locations, thereby permitting the characterization of the magnetic properties occurring across the surface of the specimen.

In accordance with one aspect of the present invention, a magnetic inspection probe is provided for measuring the magnetic properties in an anisotropic test specimen by taking a single reading of magnetic parameters in at least two directions oriented in a known manner to one another across the surface of the specimen.

The magnetic inspection probe comprises means for introducing a magnetic field into the test specimen, means for measuring the magnetic flux within the test specimen and means for measuring the resultant magnetic field intensity adjacent to the surface of the test specimen in multiple directions.

In accordance with another aspect of the present invention a method for determining in-plane anisotropy in magnetic properties across the surface of the test specimen is provided. This method comprises the steps of positioning the magnetic probe adjacent to the surface of the specimen, introducing a magnetic field into the specimen, measuring the flux in the specimen, measuring the magnetic field intensity in two or more directions having known relationships to one another across the surface of the specimen, and determining the values of physical properties occurring in the directions of measurement based on the measured values of magnetic flux and field intensity.

While the invention will be described and disclosed in connection with certain preferred embodiments and procedures, it is not intended to limit the invention to those specific embodiments. Rather, it is intended to cover all such alternative embodiments and modifications as fall within the spirit and scope of the invention as defined by the appended claims.

DETAILED DESCRIPTION OF THE PREFERRED EMBODIMENT

Figure 1:
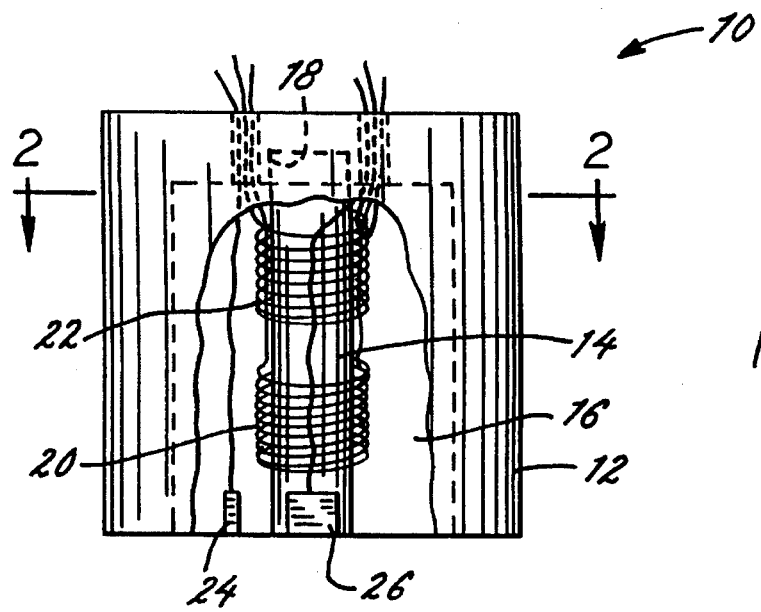
FIG. 1 is a partially cut-away side view of a preferred embodiment of the magnetic inspection probe of the present invention.
Figure 2:
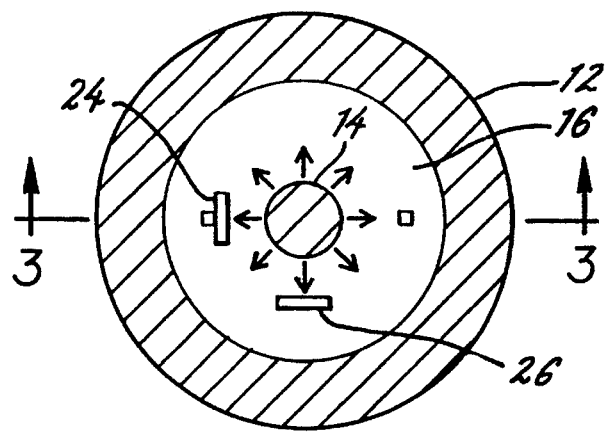
FIG. 2 is a cross sectional view of the magnetic inspection probe of FIG. 1 taken generally along line 2—2 of FIG. 1 and illustrating the radial magnetic field generated by the probe.
Figure 3:
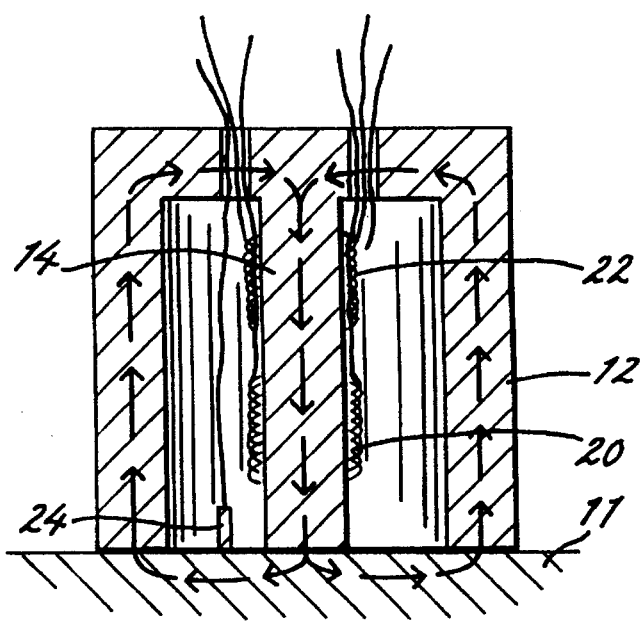
FIG. 3 is a sectional view of the inspection probe taken along line 3—3 of FIG. 2 and illustrating the flux lines in the probe and sample.

Turning now to the drawings, a preferred embodiment of the inspection probe of the present invention is illustrated in FIGS. 1–3 and designated generally by reference numeral 10. As indicated above, inspection probe 10 is particularly useful in the measurement of biaxial stress and other in-plane anisotropic properties in a sample 11 (FIG. 3) since the probe need not be reoriented with respect to the specimen surface in order to measure magnetic properties in two or more directions.

The preferred embodiment of the inspection probe 10 illustrated in FIGS. 1–3 is capable of measuring magnetic properties along two perpendicular directions of course, the probe 10 of the present invention is not limited to measurement of magnetic properties along perpendicular directions and could be configured to measure magnetic properties along any number of directions. The criteria which should be met by the probe, regardless of the directional orientation of measurement actually utilized, is that the orientation should allow characterization of the anisotropic properties occurring at the location of measurement without the need to reorient the probe to determine directional variations.

As illustrated, the inspection probe 10 preferably includes a cup-shaped outer body member 12 surrounding a central solid core 14. As illustrated most clearly in FIG. 2, core 14 is housed within the cavity formed by the cup-shaped body 12. Due to the fact that the outer diameter of the core 14 is less than the inner diameter of body member 12, an annular air gap 16 exists within the probe 10. Both the body 12 and the core 14 are preferably formed from a highly permeable magnetic material such that when the probe is placed on the surface of the sample specimen 11, the body 12 and the core 14 will form two components of a magnetic circuit which is completed by the sample specimen 11. Further, the base of the body 12 is preferably substantially planar so as to provide a good contacting relationship with the surface of the sample 11.

This contacting relationship is important due to the fact that the magnetic field which is generated by the probe is preferably both uniform and radial in nature (FIG. 2). Thus, in order to measure the effect of this field on the specimen in multiple directions, it is desirable to provide a magnetic circuit which is closed over a defined area so as to provide a clear measure of flux density resulting from the application of the radial magnetic field.

As will be recognized, the probe 10 of the present invention is not necessarily limited to the substantially cylindrical configuration illustrated and described herein but rather may be configured in any suitable geometry. While no dimensional or geometric restraints are placed on the invention, in the preferred embodiment, the core 14 will be a solid cylindrical rod with a diameter of approximately 0.500 inches and a length of approximately 1.875 inches. As illustrated, the body portion 12 will preferably be of a substantially hollow cylindrical configuration with an inner diameter of approximately 1.000 inches, an outer diameter of approximately 1.500 inches, and a total height of approximately 2.000 inches.

In the preferred embodiment, the central bore of body portion 12 is approximately 1.750 inches deep with a smaller diameter counter bore 18 sunk approximately an additional 0.125 inches into the top for insertion of core 14. Once core 14 is inserted into counter bore 18, permanent attachment can be made by any convenient adhesive means such as are known in the art. It will be appreciated that the probe of the present invention is not limited to a configuration in which the core and body are separate elements. Rather, the probe of the present invention could also be formed from a unitary one-piece construction by means of casting, machining or other processes as are well known to those of skill in the art.

Both the cup-shaped body 12 and the central core 14 are preferably composed of a highly permeable ferromagnetic material so that the flux is substantially sustained within the magnetic circuit formed by the inspection head. While many such materials can be used, one material which has proven to be particularly suitable is pure (or "soft") iron. This material is marketed by Armco Steel Corporation of Middletown, Ohio as Armco iron.

Core 14 is preferably wrapped with two coils 20, 22. Coil 20 is a power coil used to generate the radial magnetic field. The flux lines produced in sample 11 by introduction of this magnetic field are illustrated in FIG. 3. Power coil 20 may be powered by any appropriate power supply means including a variable bipolar power supply such as those well known in the art. As will be recognized by those skilled in the art, the use of a variable power supply permits the magnetic field strength to be altered and cycled in a controlled manner as described in U.S. Pat. No. 5,006,621 to Jiles, thereby permitting the collection of data of magnetic flux and field for each change in magnetic field strength to generate a full hysteresis loop.

Through generation of such a hysteresis loop a full range of magnetic properties can be determined for each location of measurement. Moreover, due to the ability to measure these magnetic properties in two or more directions, anisotropy of magnetic properties can be identified at any location of measurement. Further, since a full hysteresis loop can be generated for both directions, a comprehensive evaluation of the magnetic properties occurring across the surface of a sample can be obtained by taking measurements at multiple locations across the surface, thereby allowing any variation in properties to be mapped across the sample.

Coil 22 is a flux coil used to measure flux density in the specimen. Coil 22 will typically be connected to a fluxmeter (not shown) which will generate an analog voltage signal having a magnitude related to the measured flux.

As previously indicated, the probe 10 is capable of measuring the magnetic properties in an anisotropic specimen by taking a reading in at least two directions which have a known orientation with respect to one another. Thus, as best illustrated in FIG. 2, probe 10 also preferably includes two Hall probes 24, 26 located within the air gap 16 between cup body 12 and core 14. Alternative field sensing devices can, of course, also be utilized and are considered to be within the scope of the present invention. The Hall probes are preferably connected to a Gaussmeter (not shown) capable of accepting multiple inputs, although a separate Gaussmeter could be used for each field sensing device.

Importantly, Hall probes 24, 26 are preferably positioned at approximately a 90 degree angle to each other, thereby accomplishing the measurement of the magnetic field in two orthogonal directions across the sample surface. By simultaneously measuring the flux in the specimen and the resultant magnetic field adjacent the specimen surface in two known directions, a direct measure of in-plane anisotropy can be obtained based on the known relationships between the measured magnetic properties and the physical characteristics of the material.

The probe 10 of the present invention may be used to measure in-plane anisotropy with respect to a number of physical characteristics. For example, once the measurements are taken, biaxial stress components can be quantified by means of the method disclosed in U.S. Pat. No. 5,012,189 to Jiles. Moreover, the probe 10 of the present invention may be incorporated in place of the magnetic field device of the system disclosed in U.S. Pat. No. 5,008,621 or any other appropriate system, thereby permitting directional measurements to be taken of multiple magnetic parameters without the need to reorient the probe during measurement.

As illustrated in FIG. 3, during operation the probe 10 of the present invention is placed on a specimen surface 11. Power is then applied to the power coil 20 which generates two dimensional a radial magnetic field which is driven into the specimen 11. As the specimen is magnetized, the flux density of the specimen is measured by the flux coil windings 22 as the magnetic response is conveyed through body portion 12. During the magnetization of the specimen and the flux measurement, the magnetic field at the surface of the specimen is measured in at least two directions having known relations to one another. Directional variations in physical properties occurring across the surface of the specimen are then determined from the measured values of field intensity and flux density by means of known relationships between magnetic and physical properties. Moreover, as previously indicated, multiple measurements can be taken across the specimen surface to provide a comprehensive characterization of the magnetic properties which occur over the specimen surface as a whole.

In accordance with the above description, it is seen that the present invention provides an apparatus and method for measurement of magnetic properties in at least two directions without the need to remove the apparatus with respect to the surface of the sample specimen before each measurement.

We claim as our invention:

1. A magnetic inspection probe for measuring the magnetic properties of an anisotropic test specimen by making magnetic measurements in at least two directions oriented in a known manner to one another across the surface of the test specimen without the need to reorient the probe, the inspection probe comprising:

the probe having a body and core of respectively different shapes oriented to create a two-dimensional multi-directional magnetic field therebetween for introducing the magnetic field into the test specimen;

means for measuring the magnetic flux within the test specimen resulting from the introduction of the magnetic field; and at least two sensor means in the probe oriented in different directions with respect to each other for measuring simultaneously in two or more directions of the two-dimensional magnetic field, without reorientation of the probe, the magnetic field intensity adjacent to the surface of the test specimen caused by the introduction of the magnetic field into the specimen.

2. The probe of claim 1, wherein the means for introducing a magnetic field into the test specimen comprises a magnetizing member having an outer body portion and an inner core portion, and a coil on the inner core portion of the magnetizing member, the magnetizing member and the specimen together forming a magnetic circuit when the magnetizing member is placed on the surface of the specimen, and the coil when energized generating magnetic flux through the magnetic circuit.

3. The probe of claim 2, wherein the outer body portion of the magnetizing member is of a cylindrical cup-shaped configuration and the inner core portion is a solid cylindrical rod.

4. The probe of claim 1, wherein the means for measuring the magnetic field intensity adjacent to the surface of the test specimen comprises a plurality of Hall probes.

5. The probe of claim 4, wherein the Hall probes are disposed to measure the magnetic field intensity in two orthogonal directions.

6. A magnetic inspection probe for measuring the magnetic properties of an anisotropic test specimen by making magnetic measurement in at least two directions without the need to reorient the probe comprising:

a cylindrical cup-shaped outer body;

a solid cylindrical core centrally disposed within the cup-shaped outer body;

the core and cup defining a plane for contact with the test specimen;

power coil means disposed about the cylindrical core for generating a uniform radial magnetic field for coupling into the test specimen;

flux coil means disposed about the cylindrical core for measuring the magnetic flux density of the test specimen; and two Hall probes disposed in two directions between the cylindrical core and the outer body adjacent to the surface of the test specimen for simultaneously measuring the field intensity in said two directions without reorienting the probe.

7. A method for determining in-plane anisotropy in magnetic properties across the surface of a test specimen comprising the steps of:

(a) positioning a magnetic probe adjacent to the surface of the test specimen, the probe having a body and core of respectively different shapes oriented to produce a two-dimensional multi-directional magnetic field therebetween;

(b) energizing the probe to introduce the two-dimensional magnetic field into the surface of the test specimen;

(c) measuring via the probe the magnetic flux in the specimen;

(d) measuring using at least two sensors in the probe, the intensity of the magnetic field caused by the introduction of the magnetic field into the specimen, the measuring step being performed adjacent to the surface of the test specimen simultaneously in two or more directions which are oriented to one another in a known manner while maintaining the magnetic probe in a stationary position;

(e) altering the intensity of the magnetic field introduced in step b;

(f) repeating steps c and d for each change in the magnetic field intensity; and (g) determining the values of physical properties occurring in the directions of measurement based on the measurements of magnetic flux and field intensity adjacent to the surface of the test specimen.

8. The method of claim 7 wherein the step of energizing introduces a radial magnetic field at the surface of the test specimen in a pattern of field lines radiating out from a center point.

9. The method of claim 7 wherein the resultant magnetic field intensity is measured in two directions adjacent to the surface of the test specimen.

10. The method of claim 9 wherein stress values in two directions are determined from the measurements of magnetic flux and field intensity.

11. The method of claim 7 wherein the measurements of field intensity and flux density are carried out at a plurality of locations across the surface of the specimen thereby providing a characterization of values for physical properties and their directional variations across the surface.

12. A method for determining in-plane anisotropy in magnetic properties across the surface of a test specimen comprising the steps of:

positioning a magnetic probe on the surface of the specimen the probe having a body and core of respectively different shapes oriented to produce a two-dimensional multi-directional magnetic field therebetween;

energizing the probe to produce the two directional magnetic field and coupling the magnetic field into the surface of the test specimen via the probe;

measuring, using the probe, the magnitude of the magnetic flux introduced into the specimen;

measuring, using at least two sensors in the probe, and without reorientation of the probe, the intensity of the resultant magnetic field adjacent to the surface of the test specimen in at least two directions orientated in a predetermined relationship with respect to each other; and utilizing the flux measurements and field measurements to determine directionally varying magnetic properties to characterize the anisotropy in the magnetic properties.

13. The method of claim 12 wherein the step of energizing introduces a radial magnetic field at the surface of the test specimen in a pattern of field lines radiating out from a center point.

14. The method of claim 12 wherein the step of measuring the intensity of the resultant magnetic field includes measuring said intensity in two mutually orthogonal directions.

15. The method of claim 12 wherein the steps of energizing, measuring the flux, and measuring the field are repeated at a plurality of locations across the surface of the specimen, thereby providing a two-dimensional characterization of the in-plane anisotropy in the magnetic properties across the said surface.

* * * * *